United States Patent [19]

Schirmer

[11] 4,307,944
[45] Dec. 29, 1981

[54] MICROSCOPE

[76] Inventor: Kurt E. Schirmer, 56 Granville, Hampstead, Montreal, Quebec, H3X 3B6, Canada

[21] Appl. No.: 80,312

[22] Filed: Oct. 1, 1979

[51] Int. Cl.³ .............................................. A61B 3/10
[52] U.S. Cl. ........................................ 351/14; 351/16
[58] Field of Search ...................... 351/14, 16; 350/46

[56] References Cited

U.S. PATENT DOCUMENTS 1,475,698 11/1923 Henker ................................... 351/14
3,591,262 1/1969 Gambs ................................... 351/14

Primary Examiner—John K. Corbin
Assistant Examiner—Rodney Bovernick
Attorney, Agent, or Firm—Swabey, Mitchell, Houle, Marcoux & Sher

[57] ABSTRACT

A microscope which is suitable for slit-lamp microscopy of the fundus without contact lens, stereochronoscopy, and laser photo-coagulation in the fundus and the anterior segment of the eye, is provided having two telescopic sections, the first section having an objective lens capable of projecting by rectangular projection the three-dimensional image of the fundus of an eye in the microscope. A reticle is provided a predetermined distance from the objective lens within the microscope such that when the microscope is properly aligned with the eye, the reticle will be in the plane of the image of pupil projection in the image of the eye. The second telescopic section has a field lens and viewing apparatus and a reticle means spaced from the field lens such that it will be at the focal point of the field lens. Slit-lamp means are provided on the second tubular section such that it will project a slit-lamp beam focused at the focal point of the field lens. A laser beam projection apparatus can also be attached to the second tubular section such that its wide beam will be projected and focused at the focal point on the aerial image of the field lens.

6 Claims, 2 Drawing Figures

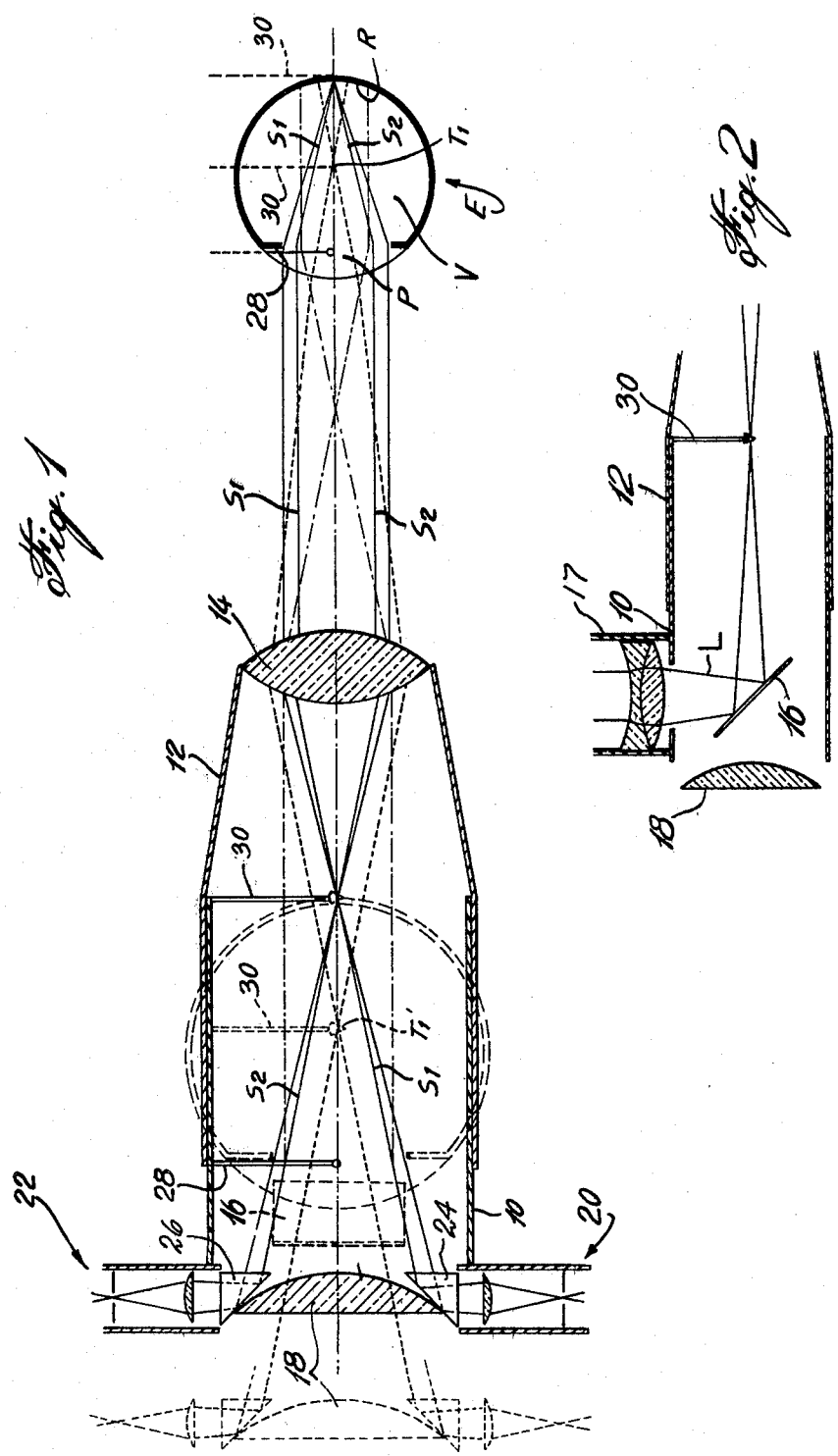

MICROSCOPE

BACKGROUND OF THE INVENTION

1. Field of the Invention

The present invention relates to the field of ophthalmology, and more particularly, to a microscope suitable for slit-lamp microscopy for fundus examination for diagnosis and surgery, stereo-chronoscopy, and for laser photo-coagulation.

2. Description of the Prior Art

In the case of present slit-lamp microscopy, a plano-concave contact lens must be used. The field of vision is limited to the diameter of the pupil and the depth of the virtual image is undesirably reduced. Further, present day slit-lamp microscopes for surgery are relatively inflexible and result in having to align and set the patient's eye to the instrument rather than the opposite.

SUMMARY OF THE INVENTION

The microscope permits slit-lamp microscopy within the eye without the need of using a contact lens for extended vitrectomy surgery which is ultimately traumatic to the patient.

It is an aim of the present invention to provide a microscope in which the three-dimensional image space of the eye can be accurately projected by rectangular projection and in which the distance of the microscope from the eye can be accurately located by means of predetermined references so as to enhance stereo-chronoscopy of the eye.

It is a further aim of the present invention to provide slit-beam illumination in such a microscope whereby accurate stereotaxis of the object space can be made.

It is still a further aim of the present invention to provide a microscope in which wide aperture laser beam treatment can be provided accurately within the fundus of the eye with little focal depth, thereby limiting the effect of the laser treatment to the focal point of the treatment in depth.

A construction in accordance with the present invention includes a microscope having a first telescopic section and a second telescopic section, the first telescopic section mounting a fixed objective lens and first reticle means at a predetermined distance from the objective lens for coincidence with the image of the pupil of an eye to be observed, the second tubular telescopic section mounting the viewing apparatus including a field lens, a second reticle means fixed in the second section relative to the field lens such that the second reticle means is at a focal point of the field lens and the second tubular section can be adjusted relative to the first section to focus on an object target within the eye while the first reticle means is coincident with the image of the pupillary plane of the eye.

In a more specific embodiment of the present invention, at least one slit-lamp device is provided and is associated with the second tubular section of the microscope and the slit-lamp beam is focused at the focal point of the field lens and will illuminate the object target in the fundus of the eye.

In a further embodiment of the present invention, a laser beam projection means is provided fixed to the second telescopic section of the microscope in which the aperture of the device is enlarged so as to project a wide aperture laser beam into the microscope along the optical system of the microscope with a focal point at the aerial image of the field lens, such that the converging spot of the laser will be at the object target if the optical system of the microscope is focused on the object target in the fundus.

In a more specific embodiment of the present invention, a pair of slit-lamps are provided on the second section of the microscope such as to provide boundary limits for the cone of the enlarged laser beam, and both slit-lamps are on opposite sides of the microscope and are focused with the focal point at the aerial image of the field lens.

The principle of the apparatus relies on the projection of an aerial image of the fundus of the patient's eye into the space of the instrument and the combined optics with the objective lens. This is in common with fundus photography and indirect ophthalmoscopy. The space of the eye is transferred into the space of the image within the instrument in all dimensions. The third dimension, depending on the choice of the objective lens, is more magnified than the second dimension of the transversal expansion. Considering rectangular projection, the third dimension axis magnification increases proportionally with the choice of increase of the focal length objective lens which is greater than the proportional increase in the second dimension. This peculiarity can be used by the observer to his advantage by judging within the expanded depth of image space more accurately than in the compressed depth of image in contact lens microscopy. Close to the posterior pole of the emmetropic eye, this space expansion is little influenced by variations of eye to objective distance should the rectangular projection of the image be abandoned. It is however much influenced if the object target is located well within the vitreus or in the part of the retina of the same plane. Therefore to measure size and depth in well kept proportion requires the maintaining of a working distance of the combined focal lengths to achieve a rectangular projection. This control of depth expansion of the eye's image is accomplished between two preset reticles, at the focal level and at the level of the pupil. Having projected the image between these points of control by predetermined calculation, equal linear projection of objects along the third dimension axis is achieved as well as equal magnification in all segments. By observing the reticle in the pupillary plane image coincident at the pupil's midpint intermittently, the orientation of the retinal image is controlled in this system for observation and fundus photography to assure consistency of the image in sequential procedures.

If depth and diameter must be transferred proportionately from object to image space at a ratio of 1:1, the choice of focus of the objective lens in relation to that of the eye must be in the ratio of 4:3.

A slit-lamp beam focused on the retinal image level is projected into corresponding object space. Illuminating thus the retina, this fundus area will be observed as image in the image plane, slit illuminated. By expanding the telescopic tube, a level within the vitreus cavity is brought to focus. This focal point in a wide and deep field is the main point of concern for the observer, the illumination device and also for the laser beam.

BRIEF DESCRIPTION OF THE DRAWINGS

Having thus generally described the nature of the invention, reference will now be made to the accompanying drawings, showing by way of illustration, a preferred embodiment thereof, and in which:

FIG. 1 is a schematic cross-sectional view of a typical microscope in accordance with the present invention; and FIG. 2 is a fragmentary schematic view of a detail of the microscope with the section taken at right angles to the axis of the microscope shown in FIG 1.

DESCRIPTION OF THE PREFERRED EMBODIMENTS

Reference is made to the drawing which illustrates a modified ophthalmoscope having a first cylindrical tube portion 10 and a telescopic tube section 12. At one end of the telescopic tube section 12 is provided an objective lens 14. At the other end of the tube section 10, there is mounted a field lens 18 and an erecting prism (not shown) is located behind the field lens 18. The prism erects the image for a binocular (not shown).

Slit-lamp illumination devices 20 and 22 are provided on opposite sides of the telescope tube 10, and the slit-lamp beams $S_1$ and $S_2$ are adapted to enter openings in the tube 10 and to be reflected by prisms 24 and 26. These prisms in the present embodiment are illustrated adjacent to edges of the field lens 18.

A laser beam projection unit can also be connected to the telescope tube section 10 at roughly 90° to the axis of the slit-lamp beams, that is, at right angles to the plane of the schematic drawing herewith referred to.

A pupillary reticle 28 is fixed to the outer tube section 12 and is preset a distance from the objective lens 14 also fixed to the outer section 12.

A target reticle 30 is fixed to the inner tube section 10 and is, of course, a predetermined distance from the field lens 18 at the focal point thereof. The reticles 28 and 30 may be in the form of a single arrowhead pointer.

As shown in the drawing, a schematic eye E is illustrated, including the retina R, the vitreous V, and a pupil P.

When viewing a patient's eye, such as shown in the drawings, the microscope is arranged such that the pupillary reticle 28 is coincident with the plane of the image of the pupil P. The telescopic section 12 is maintained in this position fixed relative to the eye E while the inner section 10 is adapted to be moved relative to the outer tube section 12.

When viewing the fundus occuli, the image of the eye is projected within the microscope by the objective lens 14. This inverted aerial image is viewed by the observer through a stereo-binocular and erecting prism; thus, the image is viewed erect. If the object target which is to be viewed is on the retina, the inner tube section 10 is adjusted such that the reticle 30 coincides with the image of the retina R. The drawing shows this particular arrangement in full lines. As illustrated, the reticle 28 is in the plane of the projected pupil while the reticle 30 is in the plane of the projected retina. If, however, the object target $T_1$ to be viewed is in mid-vitreous, the inner tube section 10, including the binocular, is adjusted such that the reticle 30 coincides with the plane of the image to be viewed, as shown in dotted lines in the drawing. The projected target is illustrated at $T_1$ in the image plane within the tube.

It is important that accurate rectangular projection of the three-dimensional image of the eye be maintained so as to measure with facility the position of the object target $T_1$ in the space of the vitreous cavity V. A more powerful lens may be intermittently dropped across the chief ray adjacent to the field lens to ensure that the reticle 28 becomes visible in the plane of the image of the pupil. That the reticle 28 is coincident with the plane of the pupil's image ensures rectangular image projection of the eye details in the image space. Reference points can be determined in the X-Y plane considering the cardinal ray as the Z axis, such that repeated observation or photography of the eye can be properly oriented for comparison. Such reference points might be preferably the mid-point of the pupil.

The above orientation is of advantage in the field of chronoscopy in which reliance on stereoscopic vision is made to assess physical differences of details within the eye on repeated identical photography. Reference is made to chronoscopy by H. Goldmann, W. Lotmar; Graefe's Archiv Ophthalmology, volume 202, pgs. 87-99, 1977. A great deal of importance is emphasized by the authors on identical repeated photography to avoid optical disparities. These authors propose such orientation by external light sources and reflex.

A pair of slit-lamps 20 and 22 are provided on opposite sides of the Z axis of the microscope and project a slit-lamp beam into the tubular section 10 through openings provided therein onto suitably located prisms 24 and 26. These slit-lamp beams are illustrated by lines $S_1$ and $S_2$ and are adapted to be focused at the center of the reticle 30, being the target reticle. The slit-lamp beams $S_1$ and $S_2$ are then projected into the fundus through the optical system in order to illuminate the fundus. The slit-lamp, of course, will provide proper correlation of the object space to the image space and serves as a means of stereotaxis within the fundus occuli. By correlating a scale on the outer surface of the tube 10 in relation to the tube section 12, accurate adjustments of the tubes in their relative position of the slit-lamp image in the X-Y plane will enable one to determine accurately the position of the object target relative to the Z axis of the eye, that is, its distance from the retina, providing rectangular projection has been maintained.

Another way of applying the stereotaxis determination of the depth in the fundus is by fixing the tube's length and providing lens power which is added at the field lens for adjusting the observer's viewing distance, and one relies on the angularity of the slit beam in proportion to the image point's distance from the retina. The increase in this angulation and the proportionate displacement of the beam on the retina are a stereotactic measure of depth of the object target on the Z axis. By controlling the Z axis expansion of the image for rectangular projection, a constant distance between the eye and the microscope objective lens 14 is maintained, and this distance is the sum total of the combined focal lengths. Stereotactic conclusions as to the values of depth are possible.

A wide angle laser beam L can be projected from a laser device 17, from a position at 90° to the cardinal ray and be deflected by a mirror or prism 16 placed permanently or intermittently in the pathway of the viewer. The laser beam will be delimited by the slit-lamp beams and will be focused at the focal point of the field lens 18, that is, at the reticle 30. The laser beam will be used for purposes of photo-coagulation of a diseased object area. The laser beam is then, by way of the optical system, projected from this point onto the retina or object target wherein it will converge at a spot and burn the object. An aerial image of the object and the burning spot is projected back to the image plane. The spot size of the focus on the fundus is reduced in proportion to the focal length of the microscope's objective to that of the eye.

The aperture of the laser device is adjustable and easily increased. The increased aperture provides a wider beam with a greater angle of convergence, thus reducing the focal depth of the laser burn so that photocoagulation becomes limited in depth as a function of the laser device's aperture. This energy dissipation before and past the focal point avoids injury to structures closer or farther from the stereotactically determined focal point. This is important to avoid injury to eye structures other than the point of target. Unwanted penetration into deeper levels of the eye is avoided using a small spot size burn for focal treatment.

I claim:

1. A microscope comprising a first telescopic section and a second telescopic section, the first section mounting a fixed objective lens and a first reticle means at a predetermined distance from the objective lens for coincidence with the image of the pupil of an eye to be observed, the second tubular telescopic section mounting the viewing apparatus including a field lens, a second reticle means fixed in the second section relative to the field lens such that the second reticle means is at a focal point of the field lens and the second tubular section can be adjusted relative to the first section to focus on an object target within the eye while the first reticle means is coincident with the pupillary plane of the image of the eye.

2. A microscope as defined in claim 1, wherein at least one slit-lamp is mounted to the second section and the slit-lamp beam is projected such that it focuses at the focal point of the field lens coincident with the second reticle means.

3. A microscope as defined in claim 2, wherein there is at least one slit-lamp located on the side of the second telescopic section with both the slit-lamp beams being projected towards the objective lens and being focused at the focal point of the aerial image of the field lens.

4. A microscope as defined in claim 1, wherein the first reticle means acts as a reference whereby the first reticle means is aligned with the pupillary plane in the projected image of the eye and adjustment of the second telescopic section such that the second reticle in the focal point of the field lens is aligned at an object target within the image of the fundus of the eye, whereby proper stereotaxis measurements can be made in the light of rectangular projection of the image of the eye.

5. A microscope as defined in claim 2, wherein a laser beam with wide aperture providing a wide beam is projected within the second telescopic section and focused at the focal point of the field lens such that when the second telescopic section is adjusted so that the focus is on an object target within the fundus of the eye, the laser beam will converge at a spot at that focal point.

6. A microscope as defined in claim 5, wherein the slit-lamps provide boundary limits to the cone of the laser beam within the microscope as projected within the eye.

* * * * *